United States Patent [19]

Hayden

[11] Patent Number: 4,810,689

[45] Date of Patent: Mar. 7, 1989

[54] PROCESS FOR THE PREPARATION OF A CATALYST FOR THE PRODUCTION OF ALKYLENE OXIDES

[75] Inventor: Percy Hayden, Guisborough, England

[73] Assignee: Imperial Chemical Industries PLC, London, England

[21] Appl. No.: 54,784

[22] Filed: May 27, 1987

[30] Foreign Application Priority Data

Jun. 6, 1986 [GB] United Kingdom ............... 8613818

[51] Int. Cl.$^4$ .................... B01J 23/04; B01J 23/50
[52] U.S. Cl. ..................................... 502/347; 549/534
[58] Field of Search ........................... 502/347, 348

[56] References Cited

U.S. PATENT DOCUMENTS 4,207,210 6/1980 Kilty ................................ 502/348
4,356,312 10/1982 Nielsen et al. .................... 549/534
4,458,032 7/1984 Rebsdat et al. ................... 502/348
4,555,501 11/1985 Armstrong ..................... 502/348 X

FOREIGN PATENT DOCUMENTS 2045636 11/1980 United Kingdom .

*Primary Examiner*—W. J. Shine
*Attorney, Agent, or Firm*—Cushman, Darby & Cushman

[57] ABSTRACT

Silver containing catalysts for the oxidation of alkenes to alkylene oxides are produced by impregnating a support with a solution of a silver compound and an organic compound and decomposing the silver compound to silver in the presence of an alkali metal compound. Organic residues are then removed by washing and fresh alkali metal introduced.

9 Claims, No Drawings

PROCESS FOR THE PREPARATION OF A CATALYST FOR THE PRODUCTION OF ALKYLENE OXIDES

This invention relates to catalysts for the production of alkylene oxides, for example propylene oxide and preferably ethylene oxide and their production.

Catalysts for the production of olefin oxides, for example ethylene oxide by the oxidation of olefines normally comprise silver supported on a heat resisting support. The catalyst supports normally comprise of alpha alumina in the form of porous pellets into which the silver is introduced for example by impregnation of the support with a solution of a decomposable silver compound, drying and decomposing the silver compound to silver.

Silver may be introduced to a pre-formed porous heat resisting support by impregnation of the support with a solution of a silver compound, for example silver nitrate which can be reduced to silver metal if necessary by means of a reducing agent for example hydrogen. If necessary a heat treatment may be used to decompose the silver compound to silver. Suitably the impregnating solution contains a reducing agent which may be for example an anion, for example a formate, acetate, propionate, lactate, tartrate or preferably oxalate ion, of a silver compound in the solution. The reducing agent may be for example an aldehyde, for example formaldehyde or acetaldehyde or an alcohol preferably having 1 to 4 carbon atoms for example methanol or ethanol.

The solution of the silver compound may be a solution in water and/or an organic solvent, for example an aliphatic alcohol preferably having 1 to 4 carbon atoms, a polyhydric alcohol for example ethylene glycol or glycerol, a ketone for example acetone, an ether for example dioxan or tetrahydrofuran, a carboxylic acid for example acetic acid, or molten lactic acid which is preferably used in the presence of water, or an ester for example ethyl acetate or a nitrogen containing base for example pyridine or formamide or preferably an amine or diamine. An organic solvent may function as a reducing agent and/or complexing agent for the silver also.

If the silver is introduced by impregnating a support with a solution of a decomposable silver compound it is preferred that ammonia and/or a nitrogen containing base should be present. The nitrogen containing base suitably acts as a ligand maintaining the silver in solution; for example it may be pyridine, acetonitrile, an amine, especially a primary or secondary amine having 1-6 carbon atoms, and/or preferably ammonia. Other suitable nitrogen-containing bases include acrylonitrile, hydroxylamine and alkanolamines for example ethanolamine, alkylene diamines having from 2-4 carbon atoms or amides for example formamide or dimethyl formamide. The nitrogen-containing bases may be used alone or in admixture, mixtures of ammonia and a second nitrogen containing base being preferred. Suitably the nitrogen containing base or bases are used together with water. Very suitably the solution comprises silver nitrate and a lower alkyl amine having 1 or 5 carbon atoms, for example isopropylamine, in water.

When organic compounds with a reducing action are present there is a tendency to form organic deposits when the silver compound is decomposed. This may be marked if such compounds are amines. Such deposits may be removed by subsequent oxidation with molecular oxygen, but we have found that catalysts of superior performance can be obtained if such deposits are at least partly removed by washing.

We have found, however, that washing is usually not very effective because of the low solubility of the organic deposits in most solvents. We have found that if an alkali metal compound which may be cesium or rubidium but is preferably sodium or potassium and more preferably lithium is present during the decomposition of the silver compound the organic deposits are soluble to a greater degree in water, at least when amines are also present in the solution of the silver compound. It appears that this may be at least partly due to a reduction in the amount of insoluble polymeric material in the organic deposit.

Catalysts for the oxidation of alkenes to alkylene oxides may comprises an alkali metal promoter. Such catalyst are particularly valuable in the process described in our British Patent No. 2014133. In the production of such catalysts it is desirable that as much of the alkali metal should be in a chemically absorbed form as possible rather than merely being physically deposited as disclosed in our European Patent No. 85,237 and this effect is enhanced by prolonged washing of the catalyst before it is impregnated with a solution of an alkali metal and dried to introduce the alkali metal component.

This invention comprises therefore a process for the production of a catalyst for the production of alkylene oxides by oxidation of the corresponding alkene with molecular oxygen which comprises impregnating a porous, heat resisting support with a solution which comprises a silver compound and one or more organic solubilising and reducing components and decomposing the silver compound to silver in the presence of an alkali metal compound which is suitably water soluble, removing organic deposits by washing and introducing fresh alkali metal by impregnation during or after the washing stage.

If desired the depositing of the alkali metal can be carried out in the washing step by washing with a solution of an alkali metal compound. It can however be accomplished by a subsequent step of impregnating the catalyst, which step may be separated from the washing step by one or more other treatments, for example an oxidation with molecular oxygen of any remaining organic deposits on the catalyst and if desired a second wash after such air oxidation or other treatment.

The washing step or steps may be carried out with any solvent for the soluble portion of the organic deposits and should remove the major part of the soluble portion of the organic deposit. A wide range of organic solvents can be used including, for example, compounds having 1 to 10 and preferably 1 to 6 carbon atoms for example alkanols, ketones, ethers, amines, amides, chlorocompounds, carboxylic acids and esters including mono and polyfunctional compounds of these types. Water itself is however a very suitable solvent. Removal of the alkali compounds can be effected with water and the lower alkanols and polyols if it is convenient to do so or if it is wished to incorporate a different or additional alkali metal in the final catalyst to that present in the decomposition of the silver compound. The solubilizing action of the solvent may be assisted by inclusion of surface active agents, detergents and/or carboxylic acids in the solvent. example water and/or a C1 to C4 alkanol and/or C1 to C4 amine. Preferably water or water with an alkanol is used, and the water content of the solvent is preferably at least 70% by weight. Washing is suitably carried out at a temperature in the range 20–150° C. and preferably 20° to 100° C. at elevated pressure if necessary to prevent vapourisation of the solvent.

The washing liquid, time and temperature should be selected to remove the major part of the soluble organic residues and preferably also of the alkali metal compound.

Without wishing to be bound by any theory, it is believed that apart from simple dissolution or organic deposits, reactions with the solvent, for example hydrolysis of the deposits may occur.

Suitably the atomic ratio of alkali metal to silver during the decomposition step is 0.01 to 2 and preferably 0.05 to 1 and more preferably 0.1 to 0.8.

If desired a pyrolysis stage may be carried out after washing and before the introduction of fresh alkali metal to improve the stability of the catalyst, that is, to reduce the decline in performance of the catalyst with time when it is in use. This may comprise an oxidation stage or a non-oxidative heat treatment stage.

Any oxidation stage should be carried out under conditions which do not affect the silver deposit adversely; at maximum temperature of 200° to 400° C. the oxidation time is not particularly critical and may be several hours but at high temperatures up to 700° C. the residence times must be short, a typical residence time at 700° C. being at most a few minutes or even seconds.

Instead of an oxidation stage, a heat treatment stage may be carried out in an inert atmosphere, for example CO2 or preferably nitrogen, argon or the like. Temperatures may be used similar to those of an oxidation stage as aforesaid, but times of exposure are less critical in this case and may be for example 30 minutes to 30 hours and preferably 1 to 20 hours at temperature of 500° to 700° C. The heat treatment stage is preferably carried out after washing and either after or preferably before introducing fresh alkali metal. More than one heat treatment stage may be employed.

Depositing the alkali metal may be carried out according to the procedures of our European Patent No. 85237 which discloses a process for improving the performance of a catalyst for the production of alkylene oxides by the reaction of the corresponding alkene with oxygen, which comprises silver supported on an Alpha-alumina support which comprises introducing an alkali metal selected from lithium, sodium, rubidium and/or preferably potassium to the catalyst in a ratio of one part chemically absorbed (adsorbed) to at most three preferably at most two and more preferably at most one part physically deposited, by contacting the catalyst with a solution or colloidal solution of a compound of lithium, sodium, rubidium, and/or preferably potassium in a solvent which has a dielectric constant of at most 15 preferably at most 8 and more preferably at most 5 at 20° C. The dielectric constants refer to those measured at low frequencies at 20° C. The solvent may be a hydrocarbon, suitably boiling in the range 50° to 250° C. at atmospheric pressure for example benzene or alkyl benzenes for example toluene or an aliphatic hydrocarbon and need not be a single compound, hydrocarbon mixtures and especially substantially aliphatic hydrocarbon mixtures preferably boiling in the range 50° to 250° C. at atmospheric pressure being preferred. If desired small quantities of alcohols, polyethers or acids preferably having at least 5 and suitably at most 20 carbon atoms per —OH group may be incorporated to assist solubility of the alkali metal compound. A similar impregnation may be carried out with cesium if desired.

The alkali metal compound is suitably a salt of a carboxylic acid preferably having at least 5 for example 5 to 20 and more preferably 7 to 12 carbon atoms per —COOH group. Suitable salts are for example octanoates such as 2-ethyl hexanoate.

By "colloidal solution" is meant a dispersion which produces a precipitation of at most 10% of the dispersed phase in the course of one day. The catalyst may be contacted with a solution or colloidal solution one or more times. Furthermore the whole process of alkali deposition i.e. impregnation and drying may be repeated to reach the preferred level and type of alkali metal content in the catalyst.

The catalyst suitably comprises at least 0.001 gram equivalents and preferably at least 0.002 gram equivalents and preferably at most 0.03 and more preferably at most 0.015 gram equivalents of the alkali metal chemically absorbed on the surface of the support per kilogram of the total catalyst. The amount of the alkali metal chemically absorbed is suitably in the range 50 to 1000 and preferably 60 to 250 parts per million per square meter per gram of support surface area. By parts per million is meant parts per million by weight potassium, lithium, sodium, cesium and/or rubidium expressed as the element based on the total weight of the catalyst.

The quantity of chemically absorbed alkali metal may be determined as follows. The catalyst may be impregnated with a solution comprising the alkali metal compound drained and dried and analysed for the alkali metal. The amount of the alkali metal deposited in the catalyst as a mere result of evaporation of the solution may be calculated from the concentration of the alkali metal component in the residual solution and the porosity of the catalyst. This gives the alkali metal content of the solution contained in the pores of the catalyst and which is incorporated in the catalyst as physically held alkali metal salt deposited by evaporation of the solution. The excess alkali analysed to be in or on the catalyst over and above this figure is the chemically adsorbed alkali metal. An alternative method of determining the chemically adsorbed alkali metal is to wash the catalyst with the impregnating solvent, which removes only physically held alkali metal and then with water which removes the more strongly held chemically absorbed alkali metal. The quantity of alkali metal removed in the second step is that which had been chemically adsorbed. A further alternative method is to measure the depletion of alkali metal compound from the impregnating solution which, together with knowledge of the volume of the impregnating solution enables an evaluation of the more strongly held chemically absorbed alkali metal to be made.

The weakly held alkali metal compound may be selectively or partially selectively removed by washing of the alkali metal impregnated catalyst with a solvent having a dielectric constant in the range 5 to 35 preferably 10 to 30.

The porous heat resisting support preferably has a specific surface area in the range 0.05 to 10 m$^2$/g and preferably 1.0 to 5m$^2$/g as measured by the Brunauer Emmett and Teller method.

The catalyst support preferably has an apparent porosity as measured by the mercury absorption method of at least 205, for example 25–80% preferably 25–60% and more preferably 45–60% and mean pore diameters of 0.1 to 20 microns preferably 0.2 to 2 microns as measured by the mercury porosimetry method.

The alkali metal compound present during the decomposition of the silver compound to silver may be deposited on the support before or with the silver compound. The atomic proportion present, based on silver is suitably in the range 0.1 to 100%. When the silver compound and alkali metal are co-deposited the solution which comprises a silver compound preferably contains 3-50% of silver by weight, and a quantity of alkali metal equivalent to depositing at least 10, preferably at least 20 and more preferably at least 400 for example 1,000 to 20,000 and suitably 2,000 to 10,000 parts per million by weight on the catalyst computed from the amount of the solution absorbed in the pores of the support. The alkali metal may be present as any salt which is soluble in the solution for example the nitrate or a salt of carboxylic acid having 1 to 10 and preferably 1 to 5 carbon atoms. The alkali metal present during the decomposition of the silver compound is preferably lithium.

Impregnation may be carried out in a single stage or if desired may be repeated one or more times with intermediate drying. By this means higher silver contents of the catalyst may be achieved.

The silver compound may generally be reduced to silver by heating in the range 100° to 400° C. and preferably at most 350° C., for example for a period of 15 mins to 24 hours, preferably in the substantial absence of oxygen, for example in the presence of an inert gas for example nitrogen.

Most of the silver content of the catalyst is preferably present in the form of discrete particles adhering to the support having equivalent diameters of less than 10,000A preferably in the range 20-10,000A and more preferably 40-8,000A. By equivalent diameter is meant the diameter of a sphere of the same silver content as the particle.

Preferably at least 80% of the silver is present as particles having equivalent diameters in the aforesaid range, the quantity of silver being judged in terms of the number of particles falling in that range. The silver may be present as silver and/or silver oxide and is thought to be present normally as silver particles having an oxidised surface layer. The dimensions of the silver particles may be determined by scanning electron miscroscopy.

The catalyst preferably comprises 4 to 50% and more preferably 5 to 20% by weight of silver.

Any alkali metals initially present as components of the support in non water extractable form are ignored as they do not contribute to catalysis.

The invention also provides processes for the production of alkylene oxides for example ethylene and propylene oxides by the oxidation of the corresponding olefine with oxygen using a catalyst as aforesaid.

Partial pressures of ethylene or propylene in such processes may be in the range 0.1 - 30 and preferably 1 to 30 bars. The total pressure may be in the range of from 1 to 100 and preferably 3 - 100 bars absolute. The molar ratio of oxygen to ethylene or propylene may be in the range of 0.05 to 100. The partial pressure of oxygen may be in the range 0.01 and preferably 0.1 to 20 bars and preferably 1-10 bars. The oxygen may be supplied for example in the form of air or preferably as commercial oxygen. A diluent for example helium, nitrogen, argon and/or carbon dioxide and/or preferably methane may be present in proportions of 10-80% and preferably 40-70% by volume in total. Ethane may also be present preferably in the range 0.1-5% by volume. It is necessary to operate using gas compositions which are outside the explosive limits.

The temperature is suitably in the range 200-300° C., and preferably in the range 210-290° C. Contact times should be sufficient to convert 0.1-70%, for example 2 to 20 and preferably 5 - 205 of the ethylene or propylene and unconverted ethylene or propylene is suitably recycled.

A reaction modifier is suitably present. Suitable reaction modifiers comprise chlorine and may be for example chlorinated alkenes having 1-6 carbon atoms for example methyl chloride or tertiary butyl chloride, di-chloromethane or chloroform, a chlorinated biphenyl or polyphenyl, a chlorinated benzene which may be for example monochlorobenzene or specially vinyl chloride or ethylene dichloride. The concentration of the reaction modifier depends on its chemical nature for example in the case of ethylene dichloride 0.02 to 10 and preferably 0.05-5 parts per million by weight are normally present and in the case of vinyl chloride 0.05-20 and preferably 0.1-10 parts by million by weight are suitably present.

We have found that with appropriate concentrations of such reaction modifiers, especially vinyl chloride, attractive selectivities may be secured.

The process may suitably be carried out in the presence of a chlorine containing reaction modifier and a nitrate or nitrite forming substance in the gas phase as described in our UK Patent No. 2 014 133.

EXAMPLES

The catalyst support

In these examples catalyst support pellets comprising α-alumina containing 460 ppm w/w of silicates expressed as silicon, 88 ppm w/w sodium compounds expressed as sodium, 19 ppm w/w potassium compounds expressed as potassium, 360 ppm w/w iron compound expressed as iron and 375 ppm w/w or calcium compounds expressed as calcium, in the form of cylinders 8 mm diameter and 7.9 mm long pierced by a single hole 2-3 mm diameter were used. The mean pore diameter of the porous alumina was 1.6 microns, its water porosity was 0.42 mols per g and its surface area was 0.72 m$^2$ per g. The pellets were uniformly coated with silver metal particles as described below.

The silver solution

Silver nitrate (4,418 g) was dissolved at 70° C. into distilled water (896 ml) and the resulting solution cooled to 50° C. Monoisopropylamine (4,800 ml) was slowly added to this solution whilst stirring and cooling. The addition of the amine was sufficiently slow to avoid undue temperature rises caused by the exothermic process of complex formation between the amine and the silver salt. The temperature was maintained in the range 40° to 60° C. The resulting clear solution was cooled to room temperature its volume was measured to be 6,000 mols.

The lithium solutions

Two lithium solutions were prepared. Solution 1 comprised lithium nitrate trihydrate (3.25 g) dissolved in 2 mol of water whilst solution 2 comprised lithium nitrate trihydrate (14.40 g) dissolved in 5 ml of water.

The silver-lithium solution

Two solutions of silver and lithium nitrates were prepared. Solution 3 comprised the silver solution (188 ml) plus lithium nitrate solution 1 (2 mls). Solution 4 comprised the silver solution (184 ml) plus lithium nitrate solution 2 (5 mls).

Impregnation of the support with solution of silver nitrate

Support pellets (150 g) were evacuated before the addition of the appropriate silver nitrate solution. Three separate impregnation were performed. For catalyst 1, the silver nitrate/monoisopropylamine complex solution was used alone (194 ml). For catalyst 2, silver-lithium solution 3 (190 ml) was used. For catalyst 3, silver-lithium solution 4 (189 ml) was used.

After contacting with the solutions for 30 minutes, the impregnated pellets were separated from the residual solution and drained in each case.

Deposition of Silver

The support pellets, wet with the impregnated complex solution, were charged into a reactor. The impregnated support was heated in a stream of hot nitrogen gas, the temperature of the reactor being set at 100° C. and subsequently gradually increased from 100° C. to 300° C. over a period of 8 hours. The impregnated complex decomposed to leave particulate silver evenly dispersed on the surface of the porous-alumina pellets. The pellets also contained a residue of substances containing carbon and nitrogen. Catalysts 2 and 3 additionally contained lithium.

Conditioning the catalyst (before impregnation of potassium)

Catalysts 1, 2 and 3 were in each case contacted with a continuous flow of hot water in the temperature range 90° to 100° C. for 15 hours, cooled, drained and dried in a stream of hot nitrogen. Most of the lithium and organic and nitrogenous residues was removed.

The washed silver-coated pellets were subsequently contacted with hot air in a process which began by passing a stream of 5% air-in-nitrogen over the pellets heated at 150° C. Subsequently the air content of the gas stream and the reactor temperature were both gradually increased to 100° and 240° C., respectively. The rate of both changes were sufficiently slow as to avoid uncontrolled rises in temperature of the pellets due to the exothermicity of the process. On reaching 240° C., the pellets were contacted with the air-stream for a further 14 hours and then allowed to cool.

The resulting silver-coated pellets, now substantially free of the residues of the anaerobic decomposition process were again contacted with hot water in the temperature range 90° to 100° C. for 16 hours, then cooled, drained and dried by contacting with a stream of hot nitrogen. The products were three catalysts each characterised as a substantially clean dry dispersion of silver particles evenly coated on the surfaces, both internal and external of the porous α-alumina pellets.

Characterisation of the catalyst

The silver contents of catalysts 1, 2, and 3 were 16.2 +0.3 % w/w. The lithium extractable into 4% aqueous hydrochloric acid form catalyst 2 and 3 were less than 3 ppm.

Impregnation with potassium

Portions of each catalyst (water absorption, 0.33 ml per g; white spirit absorption, 0.34 ml per g) were impregnated with various solutions of potassium 2-ethyl hexanoate dissolved in a solvent comprising 1.3% w/w of 2-ethyl hexanol mixed with white spirit. Each portion of the catalyst was contacted with the potassium solution for 16 hours, after which the pellets were separated from the residual solution, drained and dried.

Catalysts 4, 5 and 6 were prepared by contacting catalyst 1 (14.45 g) with solutions of potassium 2-ethyl hexanoate (23.8 ml) containing 160, 190 and 249 grams of potassium per 1000 liters of solvent respectively. As evaluated from the absorbency of the pellets and the concentration of the potassium solution orginally added to the pellets, catalyst 4, 5 and 6 would have been expected to contain 54, 64 and 84 ppm w/w of potassium, respectively.

Catalysts 7, 8 and 9, respectively, were prepared similarly to catalyst 4, 5 and 6, respectively, excepting that catalyst 2 was used in place of catalyst 1.

Catalysts 10, 11 and 12, respectively, were also prepared similarly to catalyst 4, 5 and 6, respectively, excepting that catalyst 3 was used in place of catalyst 1.

Testing Catalysts 4 to 12

Each potassium-doped catalyst (5 g) was crushed and sieved to produce particulate matter in the size range 425 to 1000 microns (3 g). An aliquot (0.4 g) of the particulate matter was loaded into a middle sector of a stainless steel reactor (length, 25.4 cm; internal diameter 2 mm). The catalyst (length, 8 cm) was located in the reactor between glass beads and glass-wool plugs.

A gas mixture of ethylene (305) oxygen (8%) carbon dioxide (2.5%), ethane (0.1%), vinyl chloride (4.8 ppm), ethyl chloride (1.2 ppm) and 2-nitropropane (30 ppm) with nitrogen to balance was passed at a pressure of 16 atmospheres absolute over the catalyst. The gas was passed at a space velocity of 3600 hr$^{-1}$.

The reaction produced ethylene oxide and also some total combustion of ethylene to carbon dioxide and water.

The temperature of the reactor was adjusted to achieve 30% conversion of the oxygen fed. The latter temperature is designated $T_{30}$. It is a measure of the activity of the catalyst.

The selectivity of the catalyst, S, is the number of moles of ethylene oxide produced expressed as a percentage of the number of moles of ethylene consumed. $S_{30}$ is the selectivity at 30% conversion of oxygen.

The average result of these tests between 3 and 8 days continuous operation are tabulated below.

Catalysts 13–16

Catalyst 13 was prepared employing the methods and materials used for catalyst 4 with the differences that following the first water washing step the conditioning pyrolysis step employed nitrogen instead of mixtures of air and nitrogen and the pellets were heated to 600° C. instead of 240° C. and maintained at that temperature for 14 hours as aforesaid in the conditioning procedure and the impregnation with potassium was performed using a solution of potassium 2-ethylhexanoate containing 500 grams of potassium per 1000 liters of solution. Catalyst 14, 15 and 16 were prepared using the methods and materials used for catalyst 7 with the difference listed below. (The details of catalyst 13 are included for completeness). Pyrolysis at 600° C. was continued for 14 hours.

| Catalyst | Expected Lithium content before conditioning stages, ppm w/w | Expected Potassium Content ppm w/w | $S_{30}$ | $T_{30}$ |
|---|---|---|---|---|
| 4* | 0 | 54 | 83.0 | 251 |
| 5* | 0 | 64 | 83.0 | 254 |
| 6* | 0 | 84 | 83.6 | 257 |
| 7 | 450 | 54 | 83.0 | 241 |
| 8 | 450 | 64 | 83.2 | 241 |
| 9 | 450 | 84 | 83.5 | 246 |
| 10 | 2000 | 54 | 83.0 | 237 |
| 11 | 2000 | 64 | 83.0 | 237 |
| 12 | 2000 | 84 | 83.3 | 239 |

*Comparative examples.

| Catalyst | Lithium Solution | | Volume of Silver Solution mls | Conditioning Pyrolysis | | Potassium in impregnating solution g per 1000 l |
| | $LiNO_3, 3H_2O$ grms | Volume of water mls | | Gas | maximum Temp °C. | |
|---|---|---|---|---|---|---|
| 13 | 0 | 0 | 194 | $N_2$ | 600 | 474 |
| 14 | 23.3 | 47 | 184 | $N_2$ | 600 | 378 |
| 15 | 43.2 | 15 | 182 | $N_2$ | 600 | 287 |
| 16 | 137 | 48 | 91 | $N_2$ | 600 | 786 |

Testing Catalysts 13 to 16

This was performed according to the method used for the testing of catalysts 4 to 12 with the differences that the process gas comprised 5% of added carbon dioxide (instead of 2.5%), 5.7 ppm of vinyl chloride (instead of 4.8 ppm) and 1.3 ppm of ethyl chloride (instead of 1.2 ppm).

The conversion of oxygen was found to fall gradually through the tests. To maintain 30% conversion of oxygen and a constant rate of reaction, the reactor temperature was increased gradually throughout the test. The operating temperature at the completion of each test, all of the tests being carried out for the same period of time, as listed in $T_{30}$, final.

| Catalyst | $S_{30}$ | $T_{30}$, initial | $T_{30}$, final |
|---|---|---|---|
| 13 | 82.6 | 257 | 266 |
| 14 | 82.3 | 251 | 255 |
| 15 | 83.8 | 250 | 252 |
| 16 | 83.3 | 253 | 254 |

Catalyst 17

Catalyst 17 was prepared substantially as was catalyst 16 except potassium nitrate instead of lithium nitrate was co-impregnated with the silver solution. The limited solubility of silver and potassium nitrates in the silver-potassium solution required the silver-potassium co-impregnation to be carried out in two stages. Accordingly, following soaking the fresh support in the silver-potassium solution, the impregnated pellets were separated from the residual solution and drained. The impregnated support was then heated in a stream of hot nitrogen gas at 100° C. On drying, the pellets were impregnated with the residual solution from the first impregnation. After contacting for 30 minutes, the re-impregnated pellets were separated from the residual solution, drained, dried, and heated to 300° C., water washed, dried and pyrolised in nitrogen at 600° C. for 14 hrs, again water washed, dried and impregnated with potassium 2-ethyl hexanoate dissolved in a solvent comprising 1.3% w/w of 2-ethyl hexanol mixed with White Spirit and dried. The details are tabulated below.

| Catalyst | Potassium solution co-impregnated with silver solution | | Volume of Silver Solution mls | Conditioning Pyrolysis | | Potassium content of final impregnating solution in 2EH+/White Spirit gr 1000l |
| | $KNO_3$ grms | Volume of water mls | | Gas | Maximum Temperature °C. | |
|---|---|---|---|---|---|---|
| 17 | 19 | 217 | 182 | $N_2$ | 600 | 356 |

+2-ethyl hexanol,
14 hrs exposure at 600° C.

Testing Catalyst 17

This was performed as with catalysts 13 to 16 with the difference that the process gas comprised 6.5 ppm of vinyl chloride, 1.5 ppm of ethyl chloride, and 40 ppm of 2-nitropropane. The selectivity, $S_{30}$ was 84.9% and the temperature required to reach an oxygen conversion of 30%, $T_{30}$ was 251° C.

Catalyst 18

Catalyst 18 was prepared substantially by the procedure used for catalyst 14 except that lithium and silver oxalates were used instead of lithium and silver nitrates. Accordingly, the silver solution was made from silver oxalate (71.9 g), ethanolamine (12.7 mls), ethylene diamine (33.2 mls) and water (75 mls). The lithium solution was made from lithium hydroxide (LiOH, $H_2O$; 3.08 g), oxalic acid ($H_2C_2O_4$, $2H_2O$; 4.63 g) and water (62.5 mls). The silver-lithium solution (190 mls) was made by mixing the silver solution with the lithium solution. The procedure used to prepare catalyst 14 was then followed; that is to say, the conditioning pyrolysis was carried out in nitrogen at 600° C. and the potassium content of the impregnating solution was 378 g per 1000 mls. Testing Catalyst 18.

This was carried out according to the method used for testing catalyst 13 to 16. The result was that $S_{30}$ was 83.2% and $T_{30}$ was 264° C.

I claim:

1. A process for the production of a catalyst for the production of alkylene oxides by oxidation of the corresponding alkene with molecular oxygen which comprises impregnating a porous, heat resisting support with a solution which comprises a silver compound and one or more organic solubilising and reducing components and decomposing the silver compound to silver in the presence of an alkali metal compound, removing organic deposits by washing and introducing fresh alkali metal by impregnation during or after the washing stage.

2. A process as claimed in claim 1 in which the washing step is carried out with a solvent comprising water.

3. A process as claimed in claim 2 in which the solvent comprises water and optionally a $C_1$ to $C_4$ alkanol, at least 70% by weight of the solvent being water.

4. A process as claimed in claim 1 in which the stability of the catalyst is improved by carrying out a pyrolysis stage after washing and before the introduction of fresh alkali metal.

5. A process as claimed in claim 4 in which after pyrolysis and before the introduction of fresh alkali metal the catalyst is washed.

6. A process as claimed in claim 5 which comprises a heat treating stage in an inert atmosphere at a temperature of 200° to 700° C.

7. A process as claimed in claim 1 in which the fresh alkali metal is introduced by impregnation with a solution or colloidal solution of an alkali metal compound in a solvent which has a dielectric constant at 20° C. of at most 15.

8. A process as claimed in claim 7 in which the solution is of an alkali metal salt of a carboxylic acid having 5 to 20 carbon atoms per —COOH group in a hydrocarbon.

9. A process as claimed in claim 1 in which alkali metal compound is removed together with organic deposits by the said washing and a different alkali metal is introduced by impregnation during or after the washing stage.

* * * * *